US00PP21590P2

(12) United States Plant Patent
Pan

(10) Patent No.: US PP21,590 P2
(45) Date of Patent: Dec. 28, 2010

(54) *LANTANA* PLANT NAMED 'BAN WHIT'

(50) Latin Name: ***Lantana camara* L.**
Varietal Denomination: Ban Whit

(75) Inventor: Shifeng Pan, Hollister, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/589,233

(22) Filed: Oct. 20, 2009

(51) Int. Cl.
*A01H 5/00* (2006.01)

(52) U.S. Cl. ..... Plt./227

(58) Field of Classification Search ..... Plt./227
See application file for complete search history.

*Primary Examiner*—June Hwu
*Assistant Examiner*—Louanne C Krawczewicz Myers
(74) *Attorney, Agent, or Firm*—S. Matthew Edwards

(57) ABSTRACT

A new *Lantana* plant named 'Ban Whit,' particularly distinguished by the large sized white flowers with a golden-yellow throat, excellent floriferousness because of limited seed set, compact and dense mounding habit with medium green foliage.

1 Drawing Sheet

Latin name of the genus and species of the plant claimed: *Lantana camara* L.

Varietal denomination: 'Ban Whit'.

BACKGROUND OF THE NEW PLANT

The present invention comprises a new *Lantana*, botanically known as *Lantana camara* L. and hereinafter referred to by the variety name 'Ban Whit'.

'Ban Whit' is a product of a planned breeding program. The new cultivar 'Ban Whit' has the large sized white flowers with a golden-yellow throat, excellent floriferousness because of limited seed set, compact and dense mounding habit with medium green foliage.

'Ban Whit' originates from a hybrid cross pollination in a controlled breeding program in Gilroy, Calif. The pollination was made in June 2006 and the seed sown in December 2006. The female parent was an unpatented, proprietary plant identified as '106-1' with white flower color. '106-1' has a larger flower size, is later to flower and has fewer branches than 'Ban Whit'.

The male parent was an unpatented, proprietary plant identified as 'E36-2' with pink flower color, and a more open plant habit.

'Ban Whit' was selected as one flowering plant within the progeny of the stated cross in April 2007 in a controlled environment in Gilroy, Calif.

The first act of asexual reproduction of 'Ban Whit' was accomplished when vegetative cuttings were propagated from the initial selection in the April 2007 in a controlled environment in Gilroy, Calif.

BRIEF SUMMARY OF INVENTION

Horticultural examination of plants grown from cuttings of the plant initiated in April 2007 in Gilroy, Calif., and continuing thereafter, has demonstrated that the combination of characteristics as herein disclosed for 'Ban Whit' are firmly fixed and are retained through successive generations of asexual reproduction.

'Ban Whit' has not been observed under all possible environmental conditions. The phenotype may vary significantly with variations in environment such as temperature, light intensity and day length.

A Plant Breeder's Right for this cultivar was applied for in Canada on Jan. 30, 2009. 'Ban Whit' has not been made publicly available more than one year prior to the filing of this application.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawing shows typical flower and foliage characteristics of 'Ban Whit' with colors being as true as possible with an illustration of this type. The photographic drawing shows a flowering plant of the new variety growing outdoors in a open field trial and a close up of the flowers. These plants were grown outdoors in Gilroy, Calif. The plants were about 16 weeks of age when the photo was taken in July 2009.

DETAILED BOTANICAL DESCRIPTION

The plant descriptions and measurements were taken in Gilroy, Calif. in April 2009 on plants that were growing in 4.5 inch pots in a trial setting. These plants were about 16-18 weeks of age and were grown with several early sprays of Paclobutrazol, a plant growth regulator.

Color Chart used: Royal Horticultural Society Colour Chart (R.H.S.) 2001.

TABLE 1

DIFFERENCES BETWEEN THE NEW VARIETY 'BAN WHIT AND A SIMILAR VARIETY

| | 'Ban Whit' | 'Balucwite' (U.S. Plant Pat. No. 17,661) |
|---|---|---|
| Flower size: | Larger | Smaller |
| Flower color: | More yellow in early stage | Less yellow |
| Plant habit: | More compact/more branching | Less compact/fewer branches |
| Foliage color: | Darker | Lighter |

Plant:

*Form, growth and habit.*—Semi-woody, grown as an annual or perennial; compact and dense mounding habit; well branched.

*Plant height.*—13-14 cm.

*Plant height* (*inflorescence included*).—16-18 cm.

*Plant width.*—26-28 cm.

Foliage:

*Type.*—Opposite.

*Immature, leaf color, upper surface.*—Somewhat darker than RHS 137A.

*Lower surface.*—Closest to RHS 137B.

*Mature, leaf color, upper surface.*—Darker than RHS 147A.

*Lower surface.*—Closest to RHS 137B.

*Length.*—5.0-5.8 cm.

*Width.*—2.5-3.0 cm.

*Shape.*—Ovate.

*Base shape.*—Attenuate.

*Apex shape.*—Acute.

*Margin.*—Crenulate to serrulate.

*Texture, upper surface.*—Hispid and glandular hairs.

*Lower surface.*—Hispid and glandular hairs.

*Color of veins, upper surface.*—RHS 144A basally, otherwise indistinct.

*Color of veins, lower surface.*—RHS 144A basally, otherwise indistinct.

*Petiole color.*—RHS 144A.

*Petiole length.*—0.7-0.8 cm.

*Petiole diameter.*—0.15-0.2 cm.

*Texture.*—Hispid and glandular hairs.

Stem:

*Quantity of main branches per plant.*—4-5.

*Quantity of leaves per branch.*—6-8.

*Color of stem.*—Closest to RHS 144A but a little lighter.

*Length of stem.*—11-16 cm.

*Diameter.*—0.2-0.3 cm.

*Length of internodes.*—0.5-2.0 cm.

*Texture.*—Hispid and glandular hairs.

Inflorescence:

*Type.*—Umbel like, flattened semi-sphere the florets are sessile on an ovate receptacle.

*Blooming habit.*—Flowers continuously from spring through fall.

*Number of flowers per inflorescence.*—10-15 open with 15-20 buds.

*Quantity of inflorescences per plant.*—25-31.

*Lastingness of individual blooms on the plant.*—About 4 weeks (depending on temperatures).

*Fragrance.*—Spicy.

*Umbel horizontal diameter.*—3.7-4.5 cm.

*Umbel vertical height.*—2.0 cm.

*Color of peduncle.*—RHS 144A.

*Length of peduncle.*—2.3-2.9 cm.

*Peduncle diameter.*—0.1-0.15 cm.

*Texture.*—Hispid and glandular hairs.

Corolla:

*Form.*—Salver-shaped to shallow cup-shaped, with a relatively long tube at the base. Each floret subtended by a single bract.

*Floret horizontal diameter.*—0.7-0.8 cm.

*Floret depth.*—1.6 cm.

*Immature, color of petals, upper surface.*—RHS 4C with RHS 14B at the corolla opening, as well as a narrow band of RHS 9A.

*Lower surface.*—RHS 13D.

*Mature, color of petals, upper surface.*—RHS 155D but much whiter, with RHS 14B at the corolla opening, as well as a narrow band of RHS 9A; finally, all flowers then show very little yellow color at the corolla opening.

*Lower surface.*—RHS 13D.

*Petal length.*—0.4-0.5 cm.

*Petal diameter.*—0.35-0.55 cm.

*Apex.*—Slightly mucronulate.

*Margin.*—Entire.

*Shape.*—Obovate.

*Degree of lobation.*—Moderate.

*Texture, upper surface.*—Papillose.

*Lower surface.*—Slightly hirsute basally.

*Corolla tube, color, outer surface.*—Closest to RHS 20D, then becoming about RHS 155D.

*Inner surface.*—RHS 155D.

*Corolla tube length.*—1.1-1.2 cm.

*Diameter* (*at opening*).—0.15 cm.

*Corolla tube texture, outer surface.*—Slightly hirsute.

*Inner surface.*—Hirsute.

Bud (just before opening):

*Color.*—RHS 12C.

*Length.*—0.7-0.9 cm.

*Width.*—0.2 at the apex.

*Shape.*—Tubular with a flared apex.

Bract:

*Color.*—RHS 146B with a slightly darker tip.

*Length.*—0.3-0.4 cm.

*Diameter.*—0.15 cm.

*Texture, upper* (*inner*) *surface.*—Glandular hairs.

*Lower* (*outside*) *surface.*—Hirsute.

Calyx:

*Number of sepals.*—5, fused sepals forming a short tube around the base of each floret.

*Color of sepals.*—RHS 145C.

*Length of sepals.*—0.3 cm.

*Width of sepals.*—0.1 cm.

*Sepal shape.*—Tube-shaped with 2 short lobes.

*Apex shape.*—Obtuse.

*Texture, upper surface.*—Hirsute; glandular hairs.

*Lower surface* (*inside*).—Glabrous.

Reproductive organs:

*Pistil.*—1.

*Length.*—0.3 cm.

*Style color.*—RHS 155B.

*Style length.*—0.25 cm.

*Stigma color.*—About RHS 1C.

*Stamens.*—4.

*Color of filaments.*—RHS 155B.

*Length filaments.*—0.6-0.7 cm.

*Anther color.*—RHS 9A.
*Length of anthers.*—0.1 cm.
*Anther shape.*—Ovoid.
*Pollen amount.*—Sparse.
*Color of pollen.*—RHS 13B.
*Fertility/seed set.*—This hybrid sets very few seeds, and those seeds were not observed for characteristics.

Disease/pest resistance: No disease/pest resistance has been observed on this hybrid.

What is claimed is:

1. A new and distinct variety of *Lantana* plant named 'Ban Whit,' substantially as illustrated and described herein.

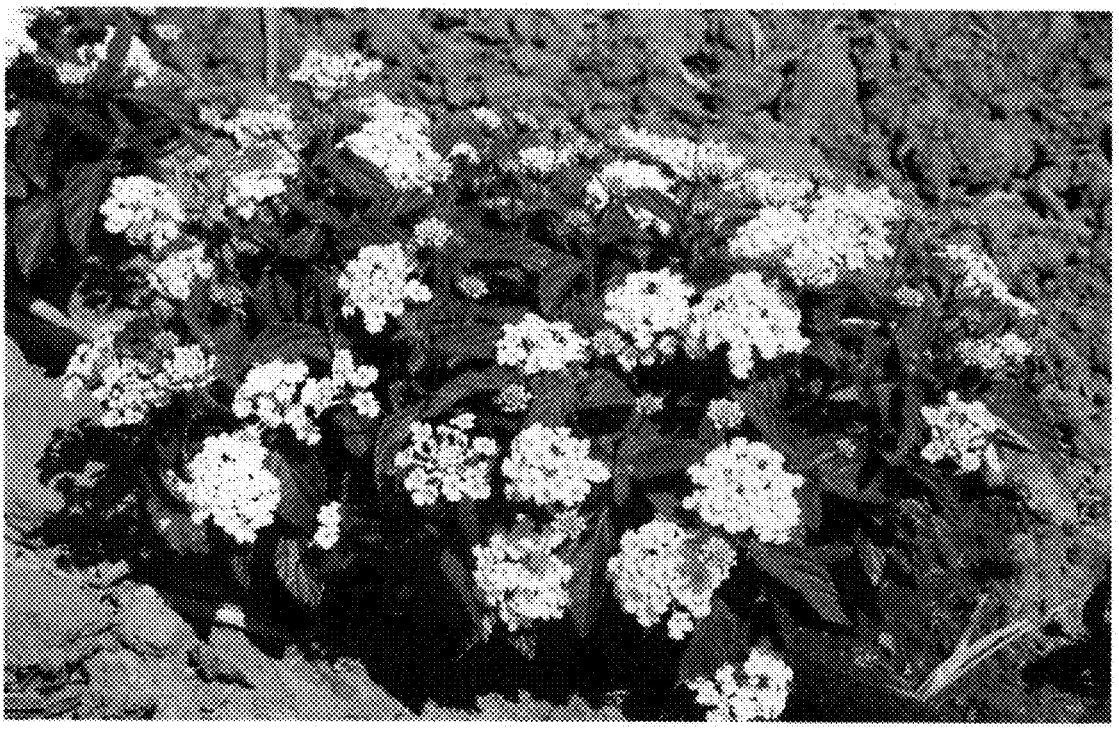
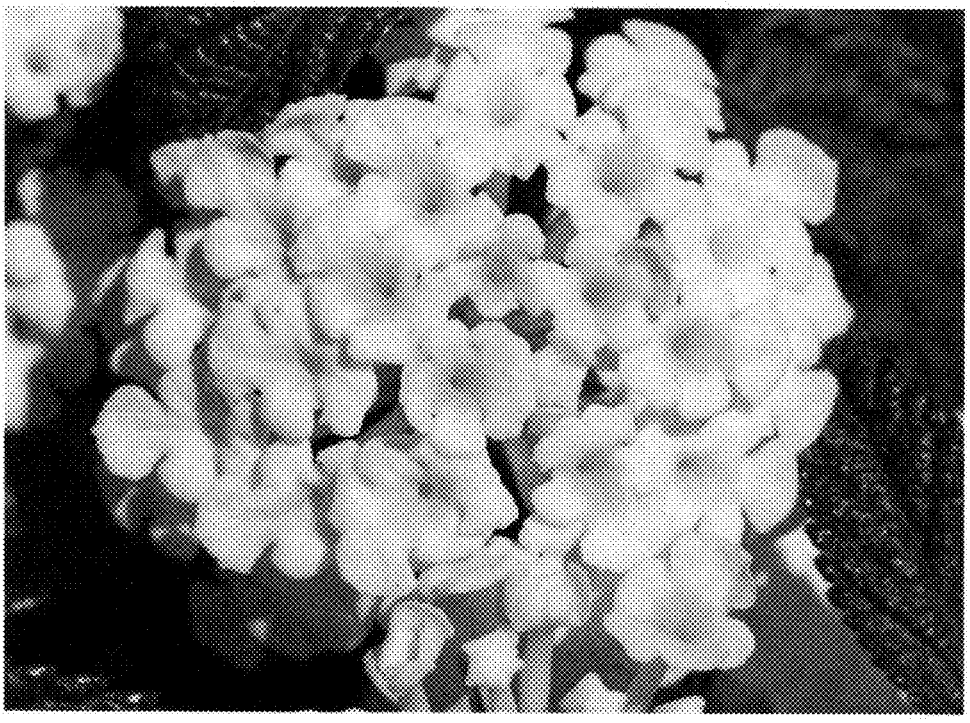

* * * * *